United States Patent [19]
Drumm et al.

[11] Patent Number: 5,602,110
[45] Date of Patent: Feb. 11, 1997

[54] METHOD AND COMPOSITION FOR TREATING CYSTIC FIBROSIS

[75] Inventors: Mitchell L. Drumm, Brecksville; Thomas J. Kelley, Mayfield Heights, both of Ohio

[73] Assignee: Case Western Reserve University, Cleveland, Ohio

[21] Appl. No.: 378,638

[22] Filed: Jan. 26, 1995

Related U.S. Application Data

[63] Continuation-in-part of Ser. No. 299,013, Aug. 31, 1994, abandoned.

[51] Int. Cl.$^6$ .......... A61K 31/70; A61K 31/52; A61K 31/445; A61K 31/44
[52] U.S. Cl. .......... 514/47; 514/263; 514/264; 514/267; 514/315; 514/334; 514/851; 424/45
[58] Field of Search .......... 424/45; 514/47, 514/263, 264, 267, 315, 334, 851

[56] References Cited

U.S. PATENT DOCUMENTS

| | | | |
|---|---|---|---|
| 4,501,729 | 2/1985 | Boucher et al. | 424/45 |
| 4,851,586 | 7/1989 | Bundy et al. | 568/633 |
| 4,866,072 | 9/1989 | Edwards et al. | 514/291 |
| 4,939,169 | 7/1990 | Bundy et al. | 514/459 |
| 5,006,343 | 4/1991 | Benson et al. | 424/450 |
| 5,096,916 | 3/1992 | Skupin et al. | 514/501 |
| 5,100,647 | 3/1992 | Agus et al. | 424/45 |
| 5,110,819 | 5/1992 | Ahnfelt-Ronne et al. | 514/311 |
| 5,140,012 | 8/1992 | McGovern et al. | 514/19 |
| 5,240,846 | 8/1993 | Collins et al. | 435/240.1 |
| 5,250,286 | 10/1993 | Skupin et al. | 424/45 |
| 5,279,823 | 1/1994 | Frenz et al. | 424/94.61 |
| 5,320,962 | 6/1994 | Stiles et al. | 435/814 |
| 5,384,128 | 1/1995 | Meezan et al. | 424/450 |
| 5,434,086 | 7/1995 | Collins et al. | 436/125 |

FOREIGN PATENT DOCUMENTS

WO93/07265 4/1993 WIPO.

OTHER PUBLICATIONS

K. Sato and F. Sato, "Defective beta adrenergic response of cystic fibrosis sweat glands in vivo and in vitro", Jun., 1984, *J. Clin. Invest.*, vol. 73, pp. 1763–1771.

B. Grubb, E. Lazarowski, M. Knowles, and R. Boucher, "Isobutylmethylaxantine fails to stimulate chloride secretion in cystic fibrosis airway epithelia", 1993, *Am. J. Respir. Cell. Mol. Biol.*, vol. 8, pp. 454–460.

M. L. Drumm, J. Wilkinson, L. S. Smit, R. T. Worrell, T. V. Strong, R. A. Frizzell, D. C. Dawson, and F. S. Collins, "Chloride conductance expressed by delta F508 and other mutant CFTRs in Xenopus oocytes", Dec. 20, 1991, *Science*, vol. 254, pp. 1797–1799.

W. Dalemans, P. Dalemans, P. Barbry, G. Champigny, S. Jallat, K. Dott, D. Dreyer, R. G. Crystal, A. Pavirani, J. P. Lecocq, M. Lazdunski, "Altered chloride ion channel kinetics associated with the ΔF508 cystic fibrosis mutation", Dec. 19/26, 1991, *Nature*, vol. 354, pp. 526–528.

K. Ono, et al., "Synergistic Action of Cyclic GMP on Catecholamine–Induced Chloride Current in Guinea–Pig Ventricular Cells", 1992, *Journal of Physiology*, vol. 453, pp. 647–661.

M. Honda, et al., "Contrasting Effects of Isoproterenol and Phosphodiesterase III Inhibitor on Intracellular Calcium Transients in Cardiac Myocytes from Failing Hearts", Dec. 1994, *Clinical and Experimental Pharmacology and Physiology*, vol. 21, pp. 1001–1008.

*Primary Examiner*—Marianne M. Cintins
*Assistant Examiner*—Kevin E. Weddington
*Attorney, Agent, or Firm*—Pearne, Gordon, McCoy & Granger

[57] ABSTRACT

A method and composition for treating cystic fibrosis comprising administering to a patient a first component, a second component, and preferably a third component. The first component is an inhibitor which is specific for a cGMP-inhibited type III cAMP phosphodiesterase, preferably milrinone or amrinone; the second component is an adenylate cyclase activator, preferably forskolin, isoproterenol or albuterol; the third component is cAMP or a cAMP analog which activates protein kinase A.

17 Claims, 3 Drawing Sheets

FIG. 3A
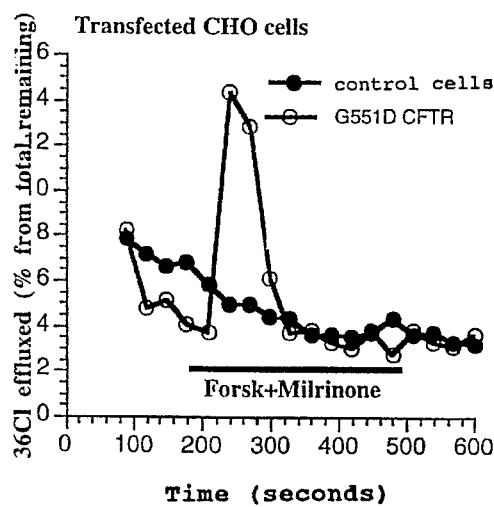
FIG. 3B
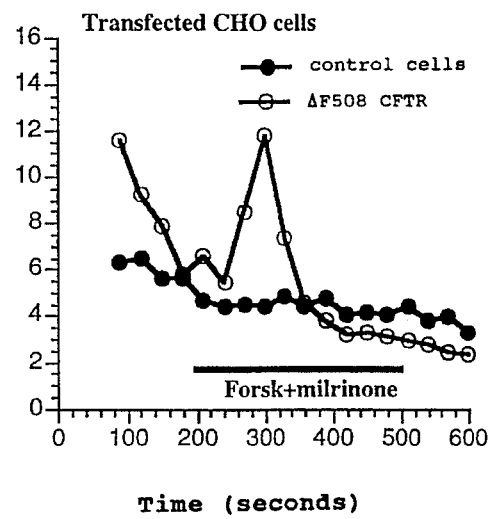
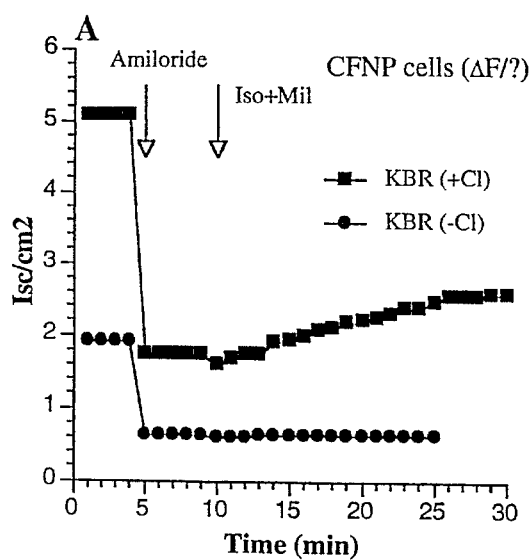
FIG. 4

METHOD AND COMPOSITION FOR TREATING CYSTIC FIBROSIS

SPONSORSHIP

Work on this invention was supported by the United States Government under Grant Nos. DK45965, HL07415, and HL50160 awarded by the National Institutes of Health. The Government has certain rights in the invention.

RELATED APPLICATION

This application is a continuation-in-part of U.S. application Ser. No. 08/299,013, filed Aug. 31, 1994, now abandoned. Its contents are incorporated herein by reference.

BACKGROUND OF THE INVENTION

The present invention relates generally to the treatment of cystic fibrosis and more particularly to the treatment of chloride secretion insufficiencies associated with cystic fibrosis by administering to a patient a therapeutically effective amount of a composition or a combination of components.

DESCRIPTION OF RELATED ART

Cystic fibrosis ("CF") is a congenital disease characterized by abnormal fluid and solute balance across the epithelia of several organs. Cystic fibrosis is the most common lethal congenital disease among caucasians where it has a prevalence of about 1 in 2000 live births.

Cystic fibrosis is a disease of secretory epithelia, tissues that mediate the transport of water, salt, and other solutes between the blood and the outside world. Epithelial cells exhibit anatomical and functional polarity. The basolateral membrane, which faces the blood, and the apical membrane, which faces the lumen (the outside world) mediate different transport events. Together they give rise to net chloride transport across the epithelium from blood to lumen. Sodium and water accompany the transport of chloride, resulting in secretion of a solution of sodium chloride into the lumen.

In cystic fibrosis, the ability of epithelial cells in the airways, sweat glands, pancreas and other tissues to secrete Cl and accompanying sodium and water is severely reduced. The clinical manifestations of CF are obstruction of airways and poor pancreatic output and are believed to be consequences of diminished secretions. The lung is usually the critical organ because thickened airway liquid appears to contribute to recurrent infection with progressive loss of ventilatory function. CF is characterized by excessively thick, dehydrated and tenacious, mucus in the airways, which leads to retention of mucus in the airways. Secretions of this nature are difficult to clear from airway surfaces and build up to obstruct airway lumens. This obstruction results in impaired respiration.

A therapeutic goal in CF is to remove retained secretions from the lung. This can be at least partially achieved by increasing salt and water transport across the epithelia into the lung, liquefying the mucus and minimizing its formation.

In 1989, the gene encoding the cystic fibrosis transmembrane conductance regulator ("CFTR") was cloned and mutations which cause CF were identified in the gene. This lead to an understanding that CFTR is a cyclic AMP ("cAMP")-dependent chloride channel found in the plasma membrane of certain epithelial cells and that CF mutations rendered the CFTR protein non-functional, or reduced its functional capacity as a chloride channel.

The most common CFTR mutation is ΔF508, which accounts for 70% of the CF chromosomes in the population. ΔF508 is a mutation in the CFTR gene resulting in a loss of phenylalanine at amino acid 508 of CFTR. It has been shown that ΔF508 CFTR could be activated in a heterologous expression system, *Xenopus laevis oocytes*, by treatment of the cells with high concentrations of 3-isobutyl-1-methylxanthine ("IBMX"), a non-specific phosphodiesterase inhibitor, and relatively low concentrations of forskolin, an adenylate cyclase activator. In 1992, Grubb et al. used IBMX in an effort to activate mutant CFTR in CF epithelial cells but were unable to activate a chloride conductance in these cells.

With regard to therapeutic approaches to improve air flow in CF patients, an attempt to improve the quality of secretions has been made, such as by utilizing aerosolized amiloride (U.S. Pat. No. 4,501,729). Similarly, see U.S. Pat. No. 4,866,072. The contents of both these patents are incorporated herein by reference. Milrinone and amrinone are known for use in treating congestive heart failure.

There is a need for a treatment for CF which activates mutant CFTR and results in increased chloride conductance across the epithelium and increased chloride secretion from epithelial cells.

SUMMARY OF THE INVENTION

A method and composition for treating cystic fibrosis in a patient is provided. The method comprises administering to the patient a treatment comprising, in combination, an amount of a first component and an amount of a second component, said first component being an inhibitor which is specific for a cGMP-inhibited type III cAMP phosphodiesterase, said second component being an adenylate cyclase activator, the amount of the first component and the amount of the second component, in combination, being a therapeutically effective treatment amount.

DESCRIPTION OF THE DRAWINGS

FIGS. 3A and 3B are a pair of graphs which illustrate chloride efflux rates of transfected Chinese hamster ovary cells under various conditions.

FIG. 4 is a graph illustrating short circuit current over time with respect to CF nasal polyp cells under certain conditions.

DETAILED DESCRIPTION OF THE PREFERRED EMBODIMENTS

Figure 1:
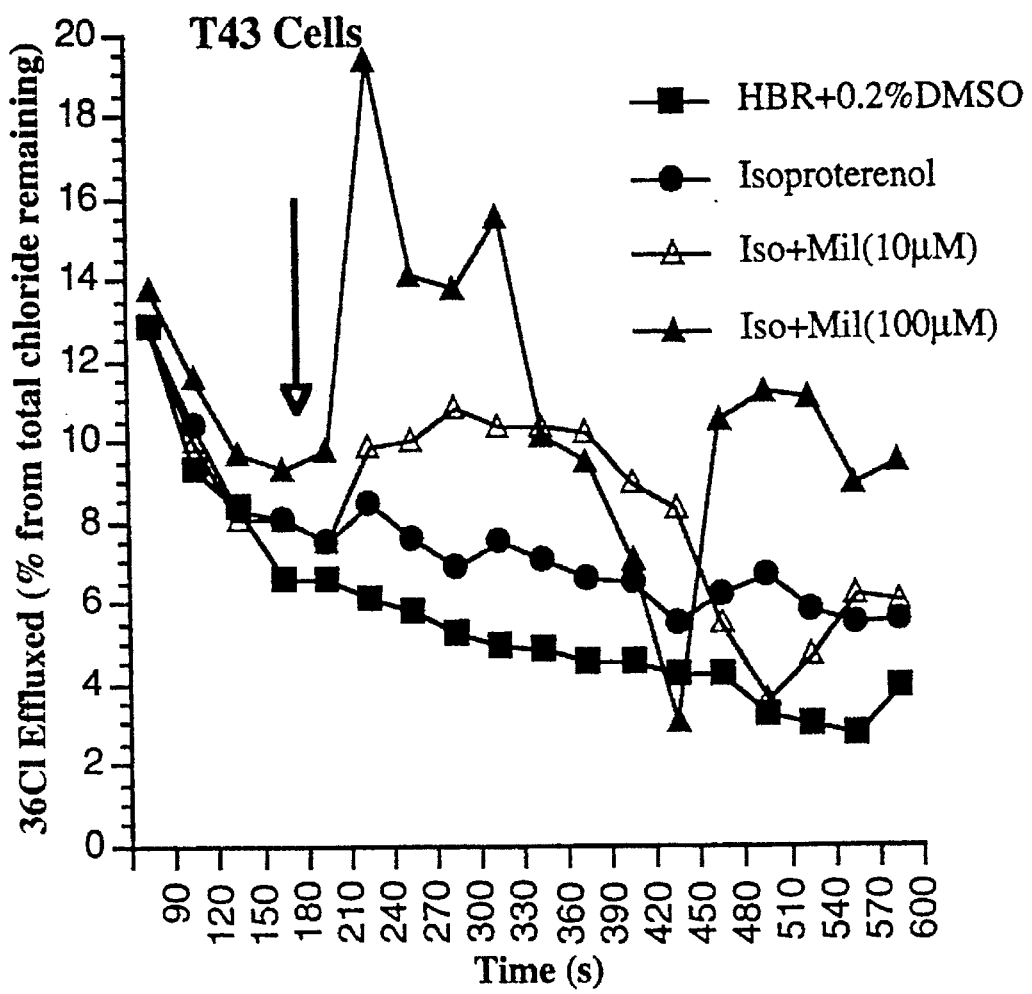
FIG. 1 is a graph illustrating chloride efflux rates of CF-T43 cells under various conditions.

The present invention includes a method and composition for treating cystic fibrosis. The method comprises administering to a patient, such as a human, suffering from cystic fibrosis a treatment comprising, in combination, an amount of a first component and an amount of a second component, said first component being an inhibitor which is specific for a cGMP-inhibited type III cAMP phosphodiesterase (sometimes referred to herein as "Type III phosphodiesterase inhibitors"), said second component being an adenylate cyclase activator, the amount of the first component and the amount of the second component, in combination, being a therapeutically effective treatment amount. As used herein in the claims, the terms or phrases "an inhibitor which is specific for a cGMP-inhibited type III cAMP phosphodiesterase", "adenylate cyclase activator", "β-adrenergic receptor agonist", "cAMP", "a cAMP analog which activates protein kinase A", and the members of these groups or classes, are defined to include their pharmaceutically acceptable derivations including pharmaceutically acceptable salts such as metal ion salts, for example alkali metal salts, and their complexes, such as when the free base complexes with a pharmaceutically acceptable acid, for example albuterol sulfate, isoproterenol hydrochloride, pirbuterol acetate, epinephrine bitartrate, isoproterenol sulfate, and terbutaline sulfate.

Inhibitors which are specific for a cGMP-inhibited type III cAMP phosphodiesterase include amrinone, milrinone, anagrelide, cilostamide, and fenoxamine.

Adenylate cyclase activators include forskolin, cholera toxin, and β-adrenergic receptor agonists. β-adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, prenalterol, procaterol, protokylol, reproterol, rimiterol, ritodrine, soterenol, salmeterol, terbutaline, tretoquinol, tulobuterol, and xamoterol.

In the practice of the present invention, the first component is preferably milrinone or amrinone and the second component is preferably forskolin or a β-adrenergic agonist, more preferably a β-adrenergic agonist selected from the group consisting of isoproterenol and albuterol. The concept or understanding of a cGMP-inhibited type III cAMP phosphodiesterase is found in or taken from *Cyclic Nucleotide Phosphodiesterases: Structure, Regulation and Drug Action*, Beavo, J. and Houslay, M. D., Eds., John Wiley and Sons (1990), particularly pp. 3–18 and 87–116.

ADMINISTRATION OF COMPONENTS

"Therapeutically effective amount" or "therapeutically effective treatment amount" generally includes the dosages set forth herein. The β-adrenergic agonists are preferably administered as aerosols; a microcrystalline suspension or solution in propellants which are inhaled, such as into the lungs, as is routinely used in the treatment of asthma. The dosage or therapeutically effective amount will depend on the particular β-adrenergic agonist used, but will preferably be in the range of 50–1000 micrograms per inhalation. Alternative administrations may be by inhalation via nebulization or by injection or orally as syrup or tablet.

For example, albuterol may be made up as a suspension of crystals, of which greater than 95% by weight are less than or equal to 10 microns in size, in a mixture of trichloromonofluoromethane and dichlorodifluoromethane, which acts as a propellant for the aerosol, a typical dosage or therapeutically effective amount or therapeutically effective treatment amount would be 90 micrograms of albuterol per inhalation. Alternatively, albuterol sulfate is dissolved at a concentration of 6 mg/ml in an aqueous solution containing benzalkonium chloride and the pH adjusted to between 3 and 5 with sulfuric acid. This solution is diluted 1 part albuterol to 5 parts normal saline for administration. The diluted solution contains 1 mg/ml of albuterol sulfate, which corresponds to 0.83 mg/ml of albuterol. This solution is administered by inhalation through a nebulizer at a rate or therapeutically effective amount of 2.5 mg of albuterol (ie, 3 ml of the diluted solution) per 5 to 10 minutes. Albuterol may also be administered at a dosage of 4 mg for adults in oral administration (syrup or tablets). All forms of delivery are preferably repeated administrations every 4 to 6 hours.

Other examples of dosages or therapeutically effective amounts: bitolterol—inhaled dose of 0.8 to 1.2 mg as a propelled aerosol, 2–3 times daily; epinephrine—inhaled dose of 0.2 to 0.4 mg as a propelled aerosol; ethylnorepinephrine—administered by subcutaneous or intramuscular injection of 1–2 mg; isoetharine—inhaled dose of 0.34 to 0.68 mg as a propelled aerosol; isoproterenol—inhaled dose of 0.13 to 0.16 mg as a propelled aerosol; metaproterenol—inhaled dose of 1.3 to 2.0 mg as a propelled aerosol; pirbuterol—inhaled dose of 0.4 mg as a propelled aerosol; salmeterol—inhaled dose of 42 micrograms as a propelled aerosol 12 hours apart; terbutaline—inhaled dose of 0.4 mg as a propelled aerosol, subcutaneous injection of 0.25–0.5 mg, 5 mg by tablet 3 times per day.

Preferably the Type III phosphodiesterase inhibitors and the other adenylate cyclase activators are also administered by aerosolization or they may be administered by inhalation via nebulization or orally as syrup or tablet. These compounds are preferably made as a suspension or solution and delivered similarly to the β-adrenergic agonists at the same or similar dosage levels. Milrinone may be prepared as a lactate salt in aqueous solution adjusted to pH 3.2 to 4 with lactic acid or sodium hydroxide with the concentration of milrinone in the solution being 1 mg/ml. The solution of milrinone may be delivered by nebulization and inhalation, at a delivery rate of 2–3 mg of milrinone per 5 to 10 minutes. The dosage range for oral delivery as syrup or tablet is believed to be similar to that of albuterol. Preparation and administration of the other Type III phosphodiesterase inhibitors is similar to that of milrinone.

The therapeutic effects of the use in combination of a Type III phosphodiesterase inhibitor and an adenylate cyclase activator are enhanced by the use of cAMP or an analog of cAMP which activates protein kinase A. Analogs of cAMP which activate protein kinase A (sometimes referred to herein as "cAMP analogs") include the following:

Sp-adenosine 3':5'-cyclic phosphorothioate 8-piperidinoadenosine 3':5'-cyclic monophosphate $N^6$, -phenyladenosine 3':5'-cyclic monophosphate 8-methylaminoadenosine 3':5'-cyclic monophosphate 8-(4-chlorophenylthio)-adenosine 3':5'-cyclic monophosphate 8-(6-aminohexyl)aminoadenosine 3':5'-cyclic monophosphate 8-bromoadenosine 3':5'-cyclic monophosphate 2'-deoxyadenosine 3':5'-cyclic monophosphate $N^6$, 2'-O-dibutryladenosine 3':5'-cyclic monophosphate $N^6$, 2'-O-disuccinyladenosine 3':5'-cyclic monophosphate $N^6$-monobutryladenosine 3':5'-cyclic monophosphate 2'-O-monobutryladenosine 3':5'-cyclic monophosphate 2'-O-monobutryl-8-bromoadenosine 3':5'-cyclic monophosphate $N^6$-monobutryl-2'-deoxyadenosine 3':5'-cyclic monophosphate 2'-O-monosuccinyladenosine 3':5'-cyclic monophosphate Preferred among the cAMP analogs are those which have a higher affinity for protein kinase A than cAMP's affinity for protein kinase A. Preferably cAMP and the cAMP analogs are also administered by aerosolization or they may be administered by inhalation via nebulization or orally as syrup or tablet at dosage levels similar to the β-adrenergic agonist dosage levels. These compounds are soluble in aqueous solutions and are preferably made as a solution in normal saline. cAMP and cAMP analogs may be prepared as a solution in normal saline at a concentration of 1 mg/ml. The solution of cAMP or cAMP analog may be delivered by nebulization and inhalation, at a delivery rate of 2–3 mg of cAMP or cAMP analog per 5 to 10 minutes. The dosage range for oral delivery as syrup or tablet is believed to be similar to that of albuterol.

Preferably, a combination of Type III phosphodiesterase inhibitor and adenylate cyclase activator, or a combination of Type III phosphodiesterase inhibitor, adenylate cyclase activator and cAMP or cAMP analog, are co-delivered or administered simultaneously (1 to 8, preferably 2 to 6 or 2 to 4, times a day) as a mixture or composition, for example similar to the way that the combinations of theophylline and ephedrine, or cromolyn and albuterol, are currently co-delivered in the treatment of asthma. For this purpose a composition or mixture may be used which contains the components, each component being present in a preselected concentration such that a portion of the composition which contains a therapeutically effective amount of one component will also contain a therapeutically effective amount of each other component. Alternatively the components may be administered separately or sequentially or in some other preselected order.

Dosages for children are generally less than dosages for adults. Nebulization solutions are preferably aqueous and preferably have about 0.1–50 mg of active ingredients per ml.

The present invention can also be used to activate or augment the efficacy of CFTR introduced to cells by recombinant DNA and gene-therapy techniques.

The method of the present invention should increase chloride secretion as a treatment for cystic fibrosis. To correct the chloride secretion defect responsible for cystic fibrosis, the above method can be applied to cystic fibrosis cells expressing mutant CFTR protein, cystic fibrosis cells expressing low levels of normal CFTR protein, or CF cells which are expressing normal CFTR as a consequence of artificial gene delivery methods (gene therapy).

EXAMPLES

1. Identification of Inhibitors of Type III Phosphodiesterases

To determine if different subtypes of cyclic nucleotide phosphodiesterases have different effects on CFTR activation, airway epithelial cells were assayed for cAMP-stimulated chloride transport in the presence of certain subtype-specific phosphodiesterase inhibitors. The nomenclature for cyclic nucleotide phosphodiesterases, as follows, is taken from Beavo (1990).

| Type | Description |
|------|-------------|
| I    | Calcium-Calmodulin dependent |
| II   | cyclic GMP-stimulated |
| III  | cyclic AMP specific-cyclic GMP-inhibited |
| IV   | cyclic AMP specific-cyclic GMP-insensitive |
| V    | cyclic GMP-specific |

Two independent cell lines, Calu-3 and 16HBE, both derived from airway epithelial cells and both expressing normal CFTR (Shen et al., 1994; Haws et al., 1994; Haws et al., 1992) were assayed for increased Cl transport either by a radioisotopic flux assay or electrophysiologically. Using the method of Venglarik et al. (1990), cells were incubated in a Ringer's solution containing $^{36}Cl$ to allow uptake of isotope into the cells, and then washed to remove external isotopic chloride. Efflux was measured by replacing the incubation solution every 30 seconds and quantitating the amount of $^{36}Cl$ secreted into it. After 6 changes of solution (3 minutes), either drugs or placebos were added to the media. The drugs added (100 μM each) were milrinone (Type III), amrinone (Type III), rolipram (Type IV), dipyridamole (Type V), and IBMX (nonspecific inhibitor). Efflux was then measured an additional 12 media changes (6 minutes). Milrinone and amrinone elicited the greatest increase in chloride efflux rate relative to rolipram, dipyridamole, and IBMX. Only the inhibitors specific for type III phosphodiesterases produced detectable increases in chloride efflux.

Whole-cell voltage clamp was used to confirm that the chloride efflux was consistent with CFTR activation. 16HBE cells were exposed to varying concentrations of milrinone and the membrane potential clamped in increments of 10 mV from −150 mV to +50 mV. The resulting current was then plotted as a function of voltage. The current/voltage relationships were linear, reversed at 0 mV for all concentrations of milrinone, and showed a reduction of current when chloride was replaced by gluconate. This showed that the effects of milrinone are dose-dependent, demonstrating a specific effect of the drug, and are consistent with activation of CFTR. A linear current/voltage relationship is a characteristic of CFTR activation. If currents are carried by chloride there should be a reduction in current at any given voltage when chloride is replaced by an ion to which CFTR is impermeante, such as gluconate.

2. Chloride Efflux Can be Stimulated in CF Cells

It is believed that the most common mutant form of CFTR, ΔF508, is poorly processed at 37° C. in mammalian cells and is consequently reduced in its ability to reach the plasma membrane, although it is believed that some does reach the plasma membrane in airway epithelial cells where it is capable of activation. It is believed that the present invention activates some or all of these mutant CFTR proteins which reach the plasma membrane. As described above, Type III phosphodiesterase inhibitors by themselves are sufficient to stimulate a chloride conductance in cells expressing normal or "wild type" CFTR. However, these Type III inhibitors, alone or by themselves, have no material or significant effect on chloride efflux from a CF epithelial cell line, CF-T43. CF-T43 is an SV40 T-antigen transformed cell line derived from a CF nasal turbinate (Jetten, et al., 1989). These cells maintain many of the original epithelial characteristics, including defective cAMP-dependant chloride transport, and have been used as a model for CF airway cells. CF-T43 cells carry and express only the ΔF508 CFTR mutation. It was also found that the β-adrenergic agonist isoproterenol had no effect on chloride efflux from the T43 cells. However, the combination of milrinone and isoproterenol generated a readily detectable chloride efflux that was dose dependent on milrinone concentration (see FIG. 1), just as the response was dose dependent in normal cells. IBMX was found to not provide an increase in efflux rate. With reference to FIG. 1, the control efflux contains Hepes-buffered Ringer's solution (HBR) +0.2% dimethylsulfoxide (DMSO), which is the concentration of DMSO in which the drugs were dissolved. The arrow indicates when the drugs were added. Iso means isoproterenol; Mil means milrinone.

3. Synergistic Effect of cAMP Analogs.

Figure 2:
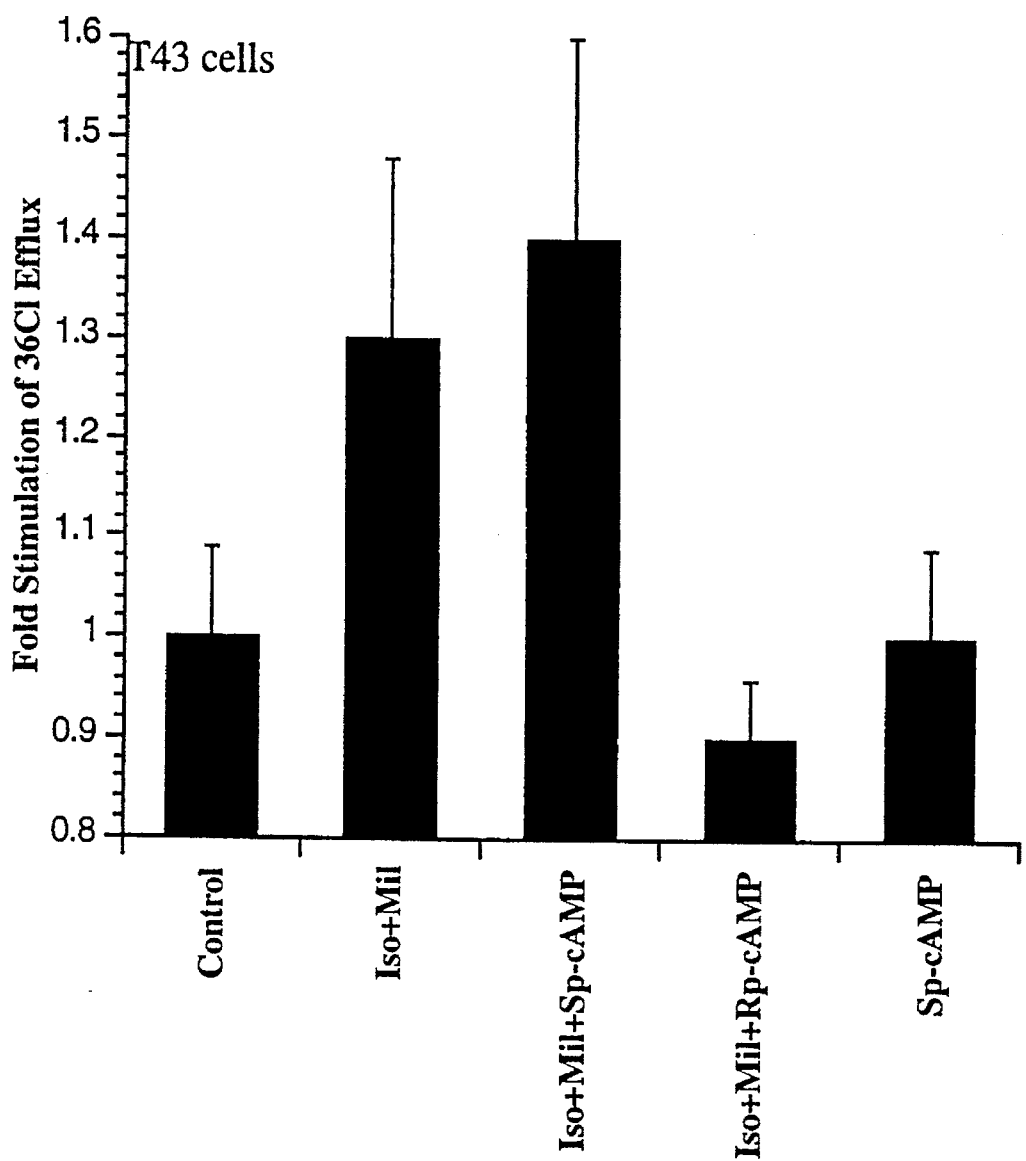
FIG. 2 is a graph comparing chloride efflux rates of CF-T43 cells under different conditions.

The effects of milrinone and isoproterenol were enhanced by the addition of Sp-adenosine 3':5'-cyclic phosphorothioate ("Sp-cAMPS"), an analog of cAMP which is known to activate protein kinase A. As shown in FIG. 2, the increased chloride efflux. Sp-cAMPS stimulated by isoproterenol and milrinone was increased by Sp-cAMPS The stereoisomer of Sp-cAMPS, Rp-cAMPS, an inhibitor of protein kinase A, abolished the increase in chloride efflux. Sp-cAMPS alone had no effect on chloride efflux. It is believed that cAMP, and other cAMP analogs which activate protein kinase A, particularly those which have a higher affinity for protein kinase A than cAMP's affinity for protein kinase A, will act synergistically similar to Sp-cAMPS.

4. Comparison of Normal and CF Cells.

The effects of isoproterenol and milrinone on chloride efflux from primary, normal epithelial cells and from the CF-T43 cell line, were compared. Normal epithelial cells were isolated from a trachea at autopsy of an adult with no history of airway disease. Normal and CF-T43 cells were plated in parallel and subjected to the chloride efflux assay. Cells were stimulated with 10 µM isoproterenol and 100 µM milrinone. Both cell types had similar responses.

5. Calcium/Calmodulin Pathway

There are at least 3 different chloride channels found in epithelial cells, including volume sensitive, calcium-dependent and cAMP-dependent. It is believed that the volume sensitive channel was not activated, since mock stimulation had no effect. To verify that the observed chloride efflux was mediated by CFTR and not by calcium-activated chloride channels, effluxes were carried out in the presence of BAPTA-AM, a chelator of divalent cations, such as calcium. The effects of calcium were examined by treating cells with a calcium ionophore, ionomycin, which induces increases in intracellular calcium, to establish how a calcium-dependant response would behave. With regard to chloride efflux, the ionomycin response was greater than the isoproterenol/milrinone response. However, the ionomycin response was eliminated by the addition of BAPTA-AM, whereas the isoproterenol/milrinone response was unchanged by BAPTA-AM. The cells were CF-T43 cells. Conversely, glibenclamide (100 µM), a known inhibitor of CFTR-mediated chloride transport, completely inhibited β-adrenergic agonist/milrinone-stimulated efflux, but had little effect on efflux elicited by ionomycin.

A test was run to confirm that the chloride efflux in primary CF cells (as opposed to CF-T43 cells used above) is mediated by the cAMP-dependent, protein kinase A pathway and not by calcium-dependent chloride channels. Efflux assays were carried out on primary CF cells, being CF nasal polyp epithelial cells homozygous for the ΔF508 mutation. Any significant contribution of calcium-activated chloride channels was ruled out by incubating the cells in BAPTA-AM, and comparing the response induced by ionomycin to that of albuterol combined with milrinone. The ionomycin-induced response was eliminated by BAPTA-AM, while the albuterol/milrinone-induced response was unaffected, as with the CF-T43 cell line above.

To confirm that chloride efflux was mediated through the cAMP/protein kinase A pathway, a similar experiment on CF nasal polyp cells was conducted using N[-2-(methylamino-)ethyl]-5-isoquinoline sulfonamide (hereinafter "H-8"), a specific inhibitor of protein kinase A. The isoproterenol/milrinone response was dramatically reduced when the cells were preincubated in H-8, indicating that efflux does require protein kinase A activity. Treatment of these cells with isoproterenol/dipyridamole (a Type V phosphodiesterase inhibitor) in the absence of H-8 did not increase chloride efflux.

Taken together, the linear current/voltage relationship (see above) and protein kinase A-dependence indicate that the type III- specific phosphodiesterase inhibitors are activating CFTR.

6. Comparison of Transformed CF Cell Lines and Primary CF Cells

Transformed cell lines often have altered properties relative to the tissues from which they were derived. To determine if the responses seen in the transformed CF-T43 cells were representative of primary tissue cells, primary epithelial cells from CF nasal polyps were assayed for chloride efflux. Tissues were obtained from nasal polypectomies of CF patients and epithelial cells were isolated by digesting cells from basement membrane by collagenase followed by low speed centrifugations. After counting viable cells, cells were plated and assayed in the same way as the CF-T43 cells. A total of 5 such experiments were performed with polyp cells from different, unrelated patients. The responses seen in these cells were quite similar to the responses of the CF-T43 cells. All but one of the patients tested carried at least one ΔF508 allele.

7. Quantitative Comparison of Primary CF Cells to Primary Normal Cells

The present invention provides that CFTR-mediated chloride permeability can be activated in CF cells by the synergistic action of an adenylate cyclase activator (such as forskolin or a β-adrenergic agonist) and a Type III phosphodiesterase inhibitor. The effects of these compounds on chloride permeability were measured as the rate of $^{36}Cl$ efflux after stimulation divided by the basal rate, given as $r_{stim}/r_{bas}$. Using transformed CF nasal polyp cells (CF-T43), primary nasal polyp cells from a CF patient, and primary human tracheal cells from non-CF individuals (normal cells), tests showed $r_{stim}/r_{bas}$ increases of 2.01 and 3.1, respectively, in the CF cells, compared to an increase of 5.5 for the normal cells, in response to isoproterenol (10 µM) and milrinone (100 µM). In the CF cells, neither agent alone elicited a rate increase. Both CF types are homozygous for the ΔF508 mutation. In contrast, the combination of isoproterenol (10 µM) and IBMX (100 µM) had no effect on chloride transport in the CF cells.

To support the belief that the observed chloride permeability is mediated by CFTR, efflux assays were carried out using 293 cells, a human embryonic kidney cell line. Chloride efflux rate was increased by adenylate cyclase activators and milrinone in cells transfected with normal and ΔF508 CFTR ($r_{stim}/r_{bas}$ =2.69 and 2.11, respectively), but not in mock transfected cells ($r_{stim}/r_{bas}$ =1.03). Although forskolin alone was sufficient to activate normal type-transfected cells, forskolin plus IBMX (100 µM) had no effect on chloride efflux in the ΔF508 transfected cells. Increased $^{36}Cl$ efflux rate was also found to be BAPTA-AM insensitive in these experiments. These data indicate the combination of an adenylate cyclase activator, such as a β-adrenergic agonist, and a Type III phosphodiesterase inhibitor, such as milrinone, is effective in activating cAMP-dependent chloride permeability in CF cells.

8. Effects of Phosphodiesterase Inhibitors and Localization of Phosphodiesterase Activity.

The effects of various phosphodiesterase inhibitors on cAMP levels were tested. Increases in cellular cAMP were measured by radioimmune assay after CF-T43 cells were incubated for 15 minutes in concentrations of phosphodiesterase inhibitor ranging from 0 to 1 mM, in the presence or absence of isoproterenol. None of the phosphodiesterase inhibitors had any significant effect on cAMP unless isoproterenol (10 µM) was included in the incubation. Isoproterenol was used in combination with the following phosphodiesterase inhibitors with the following increases in cellular cAMP over baseline: 1) rolipram (a Type IV phosphodiesterase inhibitor)—500 fold increase in cAMP over baseline; 2) RO 20-174 (a Type IV phosphodiesterase inhibitor)—240 fold increase; 3) the non-specific inhibitor IBMX - 150 fold increase; 4) milrinone—70 fold increase, which was not significantly above that of isoproterenol alone; and 5) amrinone—same as milrinone.

Isoforms of cAMP-phosphodiesterases may be found in the cytosol or in the plasma membrane. Type III phosphodiesterases, in particular, are known to have isoforms localized to either compartment. It was surprising and unexpected to find that the phosphodiesterase inhibitors milrinone and amrinone, which were the most effective at activating CFTR, gave the lowest increases in cellular cAMP, as shown above. The possibility of compartmentalization of cAMP and phosphodiesterases was then examined. To determine the localization of Type III phosphodiesterases in airway epithelial cells, cells were homogenized, and soluble and particulate fractions were separated by high speed centrifugation. The two fractions were assayed for phosphodiesterase activity and virtually all of the Type III phosphodiesterase activity, determined by amrinone or milrinone inhibition, was found in the particulate fraction, which indicates or suggests membrane localization. Because CFTR is a membrane protein, it is believed that the effect of the Type III phosphodiesterase inhibitors is due to co-localization of Type III phosphodiesterase with CFTR and/or protein kinase A in the plasma membrane. Such compartmentalization of the adenylate cyclase/cAMP/protein kinase A pathway is known to occur in cardiac myocytes and plays a role in a variety of β-adrenergic events (Buxton and Brunton, 1983; Hohl and Li, 1991), but is not believed to have been described for epithelial cells.

9. Other CF Mutations Respond to the Invention

In addition to the common CF mutation ΔF508, which accounts for about 70% of the CF chromosomes worldwide, there are over 300 other mutations in the CFTR gene which have been identified and are associated with CF. A panel of these mutants was created by site-directed mutagenesis of the CFTR cDNA and cloned into expression vectors in order to study the various mutations in a controlled and consistent environment. These constructs were transfected into Chinese hamster ovary (CHO) cells lacking a cAMP-dependent chloride conductance in order to study the ability of various mutant CFTRs to activate, relative to normal, wild type. Expression vectors containing either no CFTR (control), wild type CFTR (normal), ΔF508 or G551D CFTR (both mutants) were introduced into these cells by lipofection and the cells were assayed for chloride efflux as a response to the combination of a Type III phosphodiesterase inhibitor (milrinone) and an adenylate cyclase activator (forskolin). G551D is a mutation in the CFTR gene resulting in a substitution of aspartic acid for glycine at amino acid 551 of CFTR. As shown by FIGS. 3A, and 3B, both CF mutants (ΔF508 and G551D) gave an appreciable response above the control cells when treated with milrinone and forskolin, showing that the chloride efflux is mediated by CFTR. The control cells were transfected with a vector lacking the CFTR cDNA. The solid bar indicates when drugs were in the assay. This shows that other CF mutations can be activated by the invention.

10. Primary CF Cells Secrete Chloride Through Apical Channels in Response to the Present Invention Primary cells from a CF nasal polyp were grown as a monolayer on a permeable support and assayed for their ability to generate a short-circuit current, carried by chloride, in response to stimulation by the addition of milrinone and isoproterenol. With reference to FIG. 4, amiloride was added to the monolayer to block current mediated by sodium channels. As shown, addition of milrinone and isoproterenol stimulated an increase in current when chloride was present (squares), but not when chloride was absent (circles), indicating that the combination of milrinone and isoproterenol mediated chloride transport. The milrinone and isoproterenol were added to the apical side of the cells, consistent with the method of administration of the present invention, such as through inhalation. Thus the present invention can be administered to the apical side of CF cells to increase apical chloride conductance.

Although the preferred embodiments of this invention have been shown and described, it should be understood that various modifications and rearrangements may be resorted to without departing from the scope of the invention as disclosed and claimed herein.

What is claimed is:

1. A method of treating cystic fibrosis in a patient, comprising administering to the patient a treatment comprising, in combination, an amount of a first component and an amount of a second component, said first component being an inhibitor which is specific for a cGMP-inhibited type III cAMP phosphodiesterase, said second component being an adenylate cyclase activator, the amount of the first component and the amount of the second component, in combination, being a therapeutically effective treatment amount.

2. The method of claim 1, wherein said first component is selected from the group consisting of milrinone and amrinone and said second component is selected from the group consisting of forskolin and β-adrenergic receptor agonists.

3. The method of claim 2, wherein said second component is selected from the group consisting of isoproterenol and albuterol.

4. The method of claim 1, further comprising administering to the patient a therapeutically effective amount of a third component, said third component being cAMP or a cAMP analog which activates protein kinase A.

5. The method of claim 2, further comprising administering to the patient a therapeutically effective amount of a third component, said third component being cAMP or a cAMP analog which activates protein kinase A.

6. The method of claim 3, further comprising administering to the patient a therapeutically effective amount of a third component, said third component being cAMP or a cAMP analog which activates protein kinase A.

7. The method of claim 1, wherein said first and second components are administered simultaneously.

8. The method of claim 1, wherein said treatment is administered by aerosolization or nebulization.

9. The method of claim 4, wherein said first, second, and third components are administered by aerosolization or nebulization.

10. A composition comprising a first component and a second component, said first component being an inhibitor which is specific for a cGMP-inhibited type III cAMP phosphodiesterase, said second component being an adenylate cyclase activator.

11. The composition of claim 10, wherein said first component is selected from the group consisting of milrinone and amrinone and said second component is selected from the group consisting of forskolin and β-adrenergic receptor agonists.

12. The composition of claim 11, wherein said second component is selected from the group consisting of isoproterenol and albuterol.

13. The composition of claim 10, further comprising a third component, said third component being cAMP or a cAMP analog which activates protein kinase A.

14. The composition of claim 11, further comprising a third component, said third component being cAMP or a cAMP analog which activates protein kinase A.

15. The composition of claim 12, further comprising a third component, said third component being cAMP or a cAMP analog which activates protein kinase A.

16. The composition of claim 10, further comprising a propellant such that said composition is suitable for administration as a propelled aerosol.

17. The composition of claim 10, said composition being an aqueous solution.

* * * * *